United States Patent [19]

Drent et al.

[11] Patent Number: 5,103,043

[45] Date of Patent: Apr. 7, 1992

[54] CARBONYLATION CATALYST SYSTEM

[75] Inventors: Eit Drent; Petrus H. M. Budzelaar, both of Amsterdam, Netherlands

[73] Assignee: Shell Oil Company, Houston, Tex.

[21] Appl. No.: 672,209

[22] Filed: Mar. 18, 1991

Related U.S. Application Data

[62] Division of Ser. No. 486,993, Mar. 1, 1990, Pat. No. 5,028,576.

[30] Foreign Application Priority Data

Mar. 3, 1989 [GB] United Kingdom ............... 8904860
Aug. 18, 1989 [GB] United Kingdom ............... 8918843

[51] Int. Cl.$^5$ .............................................. C07C 67/36
[52] U.S. Cl. .................................................... 560/207
[58] Field of Search ......................................... 560/207

[56] References Cited

U.S. PATENT DOCUMENTS

| | | | |
|---|---|---|---|
| 4,124,533 | 11/1978 | Knowles et al. | 252/431 P |
| 4,739,109 | 4/1988 | Drent | 560/207 |
| 4,739,110 | 4/1988 | Drent | 560/207 |
| 4,786,443 | 11/1988 | Drent et al. | 260/549 |
| 4,940,787 | 7/1990 | Drent | 536/124 |

FOREIGN PATENT DOCUMENTS

| | | |
|---|---|---|
| 0158875 | 4/1984 | European Pat. Off. . |
| 259914 | 8/1987 | European Pat. Off. . |
| 271144 | 11/1987 | European Pat. Off. . |
| 282142 | 3/1988 | European Pat. Off. . |
| 0271144 | 6/1988 | European Pat. Off. . |
| 305012 | 8/1988 | European Pat. Off. . |
| 0305012 | 3/1989 | European Pat. Off. . |
| 386834 | 10/1989 | European Pat. Off. . |

OTHER PUBLICATIONS

Jakobsen, "NMR of Organophosphorus", J. of Molecular Spectroscopy 34, 245-256 (1970).
Kurtev, et al., Tris(2-pyridyl)phosphine Complexes of Ruthenium(ii) and Rhodium(i). Hydroformylation of Hex-1-ene by Rhodium Complexes, J. of Chem. Soc., Dalton Transactions, 1980, 55-58.
Inoguchi et al., Liganden fur extrem kurze Metall-Metall-Kontakte in Goldkomplexen, J. Mol. Spectrose, 34(2), 245-56, 1970.
Kurtev et al, "Tris(2-pyridyl)phosphine Complexes of Ruthenium(II) and Rhodium(I). Hydroformylation of Hex-1-ene by Rhodium Complexes", Journal of Chemical Society, pp. 55-58, 1979.
Inoguchi et al, "Liganden fur extre kurze Metall-Metall-Kontakte in Goldkoimplexen", Chem. Ber. 115, 3085-3095, 1982.

Primary Examiner—Paul J. Killos

[57] ABSTRACT

A catalyst system which comprises:
  a) a group VIII metal compound, and
  b) a monophosphine of formula

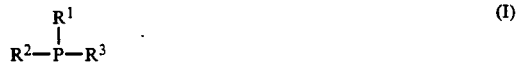

wherein $R^1$ represents an aliphatic hydrocarbyl group, $R^2$ represents an optionally substituted aromatic heterocyclic group having 5 or 6 ring atoms of which at least one is nitrogen, which may form part of an optionally substituted larger condensed ring structure, and $R^3$ 1 independently has the meaning of $R^2$ or represents an optionally substituted aryl group or an acid addition salt thereof, and their use in the carbonylation of unsaturated compounds.

9 Claims, No Drawings

CARBONYLATION CATALYST SYSTEM

This is a division of application Ser. No. 486,993, filed Mar. 1, 1990, now U.S. Pat. No. 5,028,576.

FIELD OF THE INVENTION

The invention relates to a catalyst system comprising a phosphine, to certain novel phosphines, to a process for preparing the phosphines, and to the use of the catalyst system in the carbonylation of olefins and acetylenes.

BACKGROUND OF THE INVENTION

Many processes are known in the art for the carbonylation of acetylenically and olefinically unsaturated compounds. A review of such processes is provided by J. Falbe, "New Synthesis with Carbon Monoxide", Springer-Verlag, Berlin Heidelberg New York, 1980. Typically, the processes involve the reaction of an olefinically unsaturated compound with carbon monoxide and, in some cases, hydrogen or a nucleophilic compound having a removable hydrogen atom, in the presence of a carbonylation catalyst system. In many instances, the carbonylation catalyst system comprises a Group VIII metal compound and a ligand such as phosphine.

One type of catalyst system which has been disclosed in recent years comprises a source of a Group VIII metal and a pyridyl phosphine.

Kurti Kurtev et al, *Journal of the Chemical Society, Dalton Transactions*, 1980, pages 55 to 58 disclose catalyst systems comprising a rhodium or ruthenium compound and a pyridyl monophosphine, and their use in the carbonylation of hex-1-ene.

European Patent Application Number EP-A1-0271144 discloses the use of catalyst systems comprising a palladium compound, a pyridyl monophosphine and an acid in the carbonylation of acetylenes with hydroxyl-containing compounds. Unlike EP-A1-0259914, the broadest definition of phosphines said to be suitable for use in the carbonylation process is restricted to phosphines in which all three phosphorus substituents are aromatic.

European Patent Application Number EP-A1-0282142 discloses the use of catalyst systems comprising a palladium compound, a pyridyl monophosphine and an acid in the carbonylation of olefins with hydroxyl-containing compounds. Unlike EP-A1-0259914, the broadest definition of phosphines said to be suitable for use in the carbonylation process is restricted to phosphines in which all three phosphorus substituents are aromatic.

European Patent Application Number EP-A2-0305012 discloses catalyst systems comprising a palladium compound, a pyridyl diphosphine, an acid and a quinone, and their use in the carbonylation of olefins to afford polymers.

None of the aforementioned references discloses pyridyl monophosphines in which the phosphorus atom has a simple, aliphatic substituent, nor do they suggest that such phosphines may be attractive as components for a carbonylation catalyst. Indeed, for carbonylation catalysts other than those suitable for preparing polymers; that is, carbonylation catalysts comprising a quinone; the aforementioned references clearly teach away from such phosphines.

*Chem. Ber.*, 115 (9), 3085–95 (1982) discloses methyl-di-2-pyridylphosphine and dimethyl-2-pyridylphosphine.

*J. Mol. Spectrosc.*, 34 (2), 245–56 (1970) discloses n-butyl-di-2-pyridylphosphine.

It has now been found that pyridylmonophosphines in which the phosphorus atom has a simple, aliphatic substituent, are highly effective as carbonylation catalyst components, especially in the carbonylation of acetylenes.

SUMMARY OF THE INVENTION

The present invention provides a catalyst system which comprises:
a) a group VIII metal compound, and
b) a monophosphine of formula

wherein $R^1$ represents an aliphatic hydrocarbyl group, $R^2$ represents an optionally substituted aromatic heterocyclic group having 5 or 6 ring atoms of which at least one is nitrogen, which may form part of an optionally substituted larger condensed ring structure, and $R^3$ independently is the same as $R^1$ or $R^2$ or represents an optionally substituted aryl group, or an acid addition salt thereof.

DESCRIPTION OF THE PREFERRED EMBODIMENTS

Catalyst systems according to the invention have been found to have high activity in the carbonylation of olefins and acetylenes. Outstandingly high reaction rates have been found in the carbonylation of acetylenes. Furthermore, catalyst systems according to the invention have been found to have good selectivity. With acetylenes the catalyst systems have been found to have good selectivity towards beta-carbonylated products, and with olefins, they have been found to have good selectivity towards alpha-carbonylated products. The high selectivity towards alpha-carbonylated products with olefins is particularly surprising.

Catalyst systems according to the invention which further comprise a quinone have also been found to possess activity for the carbonylation of olefinically unsaturated compounds and carbon monoxide to afford polymers.

In the phosphines of formula I, any aliphatic hydrocarbyl group conveniently has from one to thirty, preferably from one to twelve, and in particular up to 5 carbon atoms. It may be an alkenyl group such as a vinyl, allyl or butenyl group, but is preferably an alkyl group. Preferred alkyl groups are methyl, ethyl, propyl, isopropyl, 1-butyl, 2-methyl-2-propyl(t-butyl), 1-pentyl and 1-hexyl, of which those containing up to five carbon atoms are particularly preferred.

In the phosphines of formula I, at least one of the ring atoms is preferably an imino nitrogen atom.

As used herein, the term "imino nitrogen atom" means a nitrogen atom which may be represented in the structural formula of the aromatic, heterocyclic substituent containing it by the formula

For example, if the aromatic substituent is a pyridyl group, the structural formula of the aromatic substituent is

Examples of aromatic, heterocyclic substituents containing an imino nitrogen atom are pyridyl, pyrazinyl, quinolyl, isoquinolyl, pyrimidinyl, pyridazinyl, cinnolinyl, triazinyl, quinoxalinyl and quinazolinyl. Preferred substituents are pyridyl and pyrimidyl groups.

Preferably at least one of the ring atoms is an imino nitrogen atom which is separated from the phosphorus atom by one bridging carbon atom. For example, if the aromatic, heterocyclic substituent is a pyridyl group, it is preferably connected to the phosphorus atom through the carbon atom at the 2-position in the pyridyl group. Accordingly, examples of preferred aromatic, heterocyclic substituents containing an imino nitrogen atom are 2-pyridyl; 2-pyrazinyl, 2-quinolyl; 1-isoquinolyl; 3-isoquinolyl; 2-pyrimidinyl; 3-pyridazinyl; 3-cinnolinyl; 2-triazinyl; 2-quinoxalinyl; and 2-quinazolinyl. 2-Pyridyl, 2-pyrimidyl and 2-triazinyl are particularly preferred. Especially good results have been obtained when $R^2$ is an optionally substituted pyridyl group, in particular a 2-pyridyl group.

When $R^3$ does not represent one of the afore-mentioned aromatic heterocyclic groups, it represents an aliphatic hydrocarbyl group or an optionally substituted aryl group.

An optionally substituted aryl group conveniently contains not more than 18 carbon atoms in its ring system and is preferably an optionally substituted phenyl group, but may be an optionally substituted anthryl or naphthyl group.

$R^3$ preferably represents a pyridyl group, an alkyl group or an optionally substituted phenyl group.

Where in this specification, reference is made to "optionally substituted", it means a group which is either unsubstituted or substituted with one or more substituents which do not interfere with the reaction. Suitable substituents are typically selected from hydroxy, halogen (especially chloro and fluoro), alkoxy (preferably $C_{1-5}$ alkoxy, especially methoxy and ethoxy), dialkylamino (especially dimethylamino and diethylamino), mono- di- and trihalomethyl, such as trifluoromethyl, trichloromethyl and monochloromethyl, and alkyl (preferably $C_{1-5}$ alkyl group, especially methyl, ethyl, propyl, isopropyl and tert.butyl).

Examples of substituted aromatic, heterocyclic groups are 6-methyl-2-pyridyl, 6-methoxy-2-pyridyl, 3-methyl-2-pyridyl, 4-methyl-2-pyridyl and 4,6-dimethyl-2-pyridyl.

Examples of substituted aryl groups are 4-methoxyphenyl, 3-methylphenyl and 2-fluorophenyl.

Examples of phosphines of formula (I) are:
di(n-butyl)-2-pyridylphosphine,
dimethyl 2-pyridylphosphine,
methyl phenyl-12-pyridylphosphine,
n-butyl tert.butyl 2-pyridylphosphine,
n-butyl(4-methoxyphenyl)(2-pyridyl)phosphine, and
methyl di(2-pyridyl)phosphine.

Preferred acid addition salts of the phosphines of general formula (I) include salts with sulfuric acid; a sulfonic acid, e.g., an optionally substituted hydrocarbylsulfonic acid such as an optionally substituted arylsulfonic acid, e.g., benzenesulfonic acid, p-toluenesulfonic acid or naphthalenesulfonic acid, an optionally substituted alkylsulfonic acid, such as an alkylsulfonic acid, e.g., methanesulfonic acid or t-butylsulfonic acid, or a substituted aulfonic acid such as 2-hydroxypropanesulfonic acid, trifluoromethanesulfonic acid, chlorosulfonic acid or fluorosulfonic acid; a phosphoric acid, e.g., orthophosphoric acid, pyrophosphoric acid, benzenephosphoric acid or toluenephosphoric acid; a carboxylic acid, e.g., chloroacetic acid, trifluoroacetic acid, oxalic acid or terephthalic acid; or a perhalic acid such as perchloric acid.

Examples of Group VIII metals are iron, cobalt, nickel, ruthenium, rhodium, palladium, iridium and platinum.

The Group VIII metal compound is preferably selected from salts of palladium, rhodium and ruthenium, of which salts of palladium, especially divalent palladium, are preferred. Both homogeneous and heterogeneous metal compounds may be present, but homogeneous compounds are preferred. Suitable compounds are the salts of nitric acid, sulfuric acid and alkanoic acids having not more than 12 carbon atoms per molecule, e.g., acetic acid. Palladium acetate is especially preferred. Salts of Group VIII metal with any of the acids mentioned above in relation to the phosphines of formula (I) are also preferred, especially palladium salts. Moreover, metal complexes may be used, for instance, using palladium as an example, palladium acetylacetonate, tetrakis(triphenylphosphine)palladium, bis(tri-o-tolyphosphine)palladium acetate, bis(diphenylphosphine)palladium acetate, or bis(triphenylphosphine)palladium sulfate. Metal bonded on charcoal and metal bonded to an ion-exchanger, for instance an exchange resin containing sulfonic acid groups, are examples of suitable heterogeneous forms of the Group VIII metal compounds.

The catalyst systems according to the invention preferably comprise a protonic acid. It will be appreciated by those skilled in the art that when a catalyst system according to the invention comprises an acid addition salt of a phosphine of formula (I), the catalyst system inevitably comprises a protonic acid.

The function of the protonic acid is to provide a source of protons. Preferably the protonic acid is one of those referred to above in relation to the formation of acid addition salts by the phosphines of general formula (I). It may also be an acidic ion exchange resin, for example a sulfonated ion exchange resin.

When the catalyst system comprises a protonic acid, the protonic acid conveniently has a $pK_a$ (measured at 18° C. in aqueous solution) of below 6, more preferably below 4.5, e.g., below 4, most preferably below 2. The optimum $pK_a$ will depend upon the particular carbonylation reaction in which the catalyst system is to be employed.

The optimal ratio of protonic acid to phosphine will depend upon the particular carbonylation reaction in which the catalyst system is to be employed. Conveniently the number of moles of phosphine per mole of protonic acid will be in the range of from 0.1 to 50, preferably from 0.1 to 10, more preferably from 0.25 to 4.

The number of moles of phosphine of formula (I) per gram atom of Group VIII metal in the catalyst system according to the invention is not critical. It will depend upon the particular Group VIII metal and the particular carbonylation reaction. Preferably the number of moles of phosphine per gram atom of palladium is in the range of from 1 to 1,000, more preferably from 2 to 500, for example from 10 to 100.

The catalyst system according to the invention is constituted in a liquid phase. The liquid phase may conveniently be formed by one or more of the reactants with which the catalyst system is to be used. Alternatively, it may be formed by a solvent. It may also be formed by one of the components of the catalyst system.

The catalyst systems according to the invention may be homogeneous or heterogeneous. Most preferably they are homogeneous.

The catalyst systems according to the invention may be generated by any convenient method. Thus they may be prepared by combining a Group VIII metal compound, a phosphine of general formula (I) and, if appropriate, a protonic acid in a liquid phase. Alternatively, they may be prepared by combining a Group VIII metal compound and an acid addition salt of general formula (I) in a liquid phase. Alternatively, they may be prepared from a Group VIII metal compound which is a complex of a Group VIII metal with a phosphine of general formula (I), and/or a protonic acid in a liquid phase.

As has been stated above three phosphines of general formula (I) have been disclosed in *Chem. Ber.*, 115 (9), 3085-95 (1982) and *J. Mol. Spectrosc.*, 34 (2), 245-56 (1970). The remaining phosphines of general formula (I), are believed to be novel. Accordingly, the invention also provides a phosphine of general formula (I) or an acid addition salt thereof, as defined above, except for methyl-di-2-pyridyl phosphine, dimethyl-2-pyridyl phosphine, and n-butyl-di-2-pyridyl phosphine.

The phosphines of general formula (I) may be prepared by a process which comprises reacting a compound of general formula:

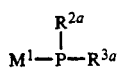
(II)

in which $M^1$ represents either a metal atom or a leaving atom or group and $R^{2a}$ and $R^{3a}$ represent two of $R^1$, $R^2$ and $R^3$ as defined above, with an appropriate compound of general formula:

(III)

in which $M^2$ represents either a metal atom or a leaving atom or group and $R^{1a}$ represents the remainder from $R^1$, $R^2$ and $R^3$ optionally followed by forming an acid addition salt.

It will be appreciated that when $M^1$ represents a metal atom, the appropriate compound of general formula (III) is one wherein $M^2$ represents a leaving atom or group. Similarly when $M^1$ represents a leaving atom or group, the appropriate compound of general formula (III) is one wherein $M^2$ represents a metal atom.

A metal atom represented by $M^1$ or $M^2$ may be any main group metal, for example an alkali metal, such as lithium, sodium or potassium; an alkaline earth metal, such as magnesium; zinc; cadmium; mercury; aluminum; gallium; indium; thallium; tin or lead. Preferably a metal atom is an alkali metal atom.

The leaving atom or group is preferably a halogen atom, most preferably a chlorine or bromine atom.

Preferably $M^2$ represents a halogen atom.

Preferably $R^{1a}$ represents $R^1$.

The reaction between the compound of general formula (II) with the compound of general formula (III) may conveniently be effected in the presence of a solvent. Suitable solvents include liquid ammonia and ethers such as tetrahydrofuran or diethyl ether, or hydrocarbons such as benzene or toluene.

The process is conveniently effected at a temperature in the range of from $-100°$ C. to $100°$ C., preferably from $-80°$ C. to $0°$ C.

An acid addition salt may conveniently be formed by contacting a phosphine of general formula (I) with an appropriate acid, preferably in the presence of a solvent.

Compounds of formula (III) wherein $M^2$ represents a metal atom may be prepared from the corresponding compounds wherein $M^2$ represents a leaving atom or group, for example a chlorine, bromine or iodine atom, by reaction with a metal alkyl, for example butyl lithium.

Compounds of formula (II) wherein $M^1$ represents a chlorine or bromine atom, may be prepared in situ from corresponding di- and tri-chloro or bromophosphines by reaction with an appropriate metal compound of formula (III).

Compounds of formula (II) wherein $M^1$ represents an alkali metal, such as lithium, may conveniently be prepared by reacting a compound of formula (II) wherein $M^1$ represents a pyridyl group with an alkali metal pyridine, alkyl, aryl or hydride. On occasion, it may be convenient to generate such compounds of formula (II) in situ, for example by reacting a halopyridine with an alkali metal alkyl to form a mixture of an alkali metal pyridine and a haloalkane, and then reacting the mixture with a bis-or tris-pyridylphosphine to afford initially the desired alkali metal alkylpyridylphosphine by reaction of the phosphide with the haloalkane. The preparation of such compounds of formula (II) is the subject of British Patent Application Number 8923683.

As has been stated above, it has been found that catalyst systems according to the invention have good activity in the carbonylation of acetylenically and olefinically unsaturated hydrocarbons.

Accordingly, the invention further provides the use of a catalyst system as defined hereinbefore in the carbonylation of an acetylenically or olefinically unsaturated hydrocarbon.

According to a further aspect, the present invention provides a process for the carbonylation of an acetylenically or olefinically unsaturated compound, which comprises reacting an acetylenically or olefinically unsaturated compound with carbon monoxide in the presence of a catalyst system as defined hereinabove.

As is well known by those skilled in the art, a very large variety of processes are known for the carbonylation of acetylenically and olefinically unsaturated compounds. Such processes can be divided into several types of reactions, depending upon the starting materials. Examples of such reactions are hydroformylation, the so called Reppe reaction, in which an unsaturated compound is reacted with carbon monoxide and a nucleophilic compound having a removable hydrogen atom; and copolymerization of an unsaturated compound with carbon monoxide.

The acetylenically or olefinically unsaturated compound is preferably an alpha olefin or acetylene.

An olefinically unsaturated compound is preferably a substituted or unsubstituted alkene or cycloalkene having from 2 to 30, preferably from 3 to 20 carbon atoms per molecule.

An acetylenically unsaturated compound is preferably a substituted or unsubstituted alkyne having from 2 to 20, especially from 3 to 10 carbon atoms per molecule.

The acetylenically or olefinically unsaturated compound may contain one or more acetylenic or olefinic bonds, for example one, two or three acetylenic or olefinic bonds.

An olefin or acetylene may be substituted by, for example, a halogen atom, a cyano group, an acyl group such as acetyl, an acyloxy group such as acetoxy, an amino group such as dialkylamino, an alkoxy group such as methoxy, a haloalkyl group such as trifluoromethyl, a haloalkoxy group such as trifluoromethoxy, an amido group such as acetamido, or a hydroxy group. Some of these groups may take part in the reaction, depending upon the precise reaction conditions. For example, lactones may be obtained by carbonylating certain acetylenically unsaturated alcohols, for example 3-butyn-1-ol, 4-pentyn-1-ol or 3-pentyn-1-ol. Thus 3-butyn-1-ol may be converted into a α-methylene-γ-butyrolactone.

Examples of alkynes are: ethyne, propyne, phenylacetylene, 1-butyne, 2-butyne, 1-pentyne, 1-hexyne, 1-heptyne, 1-actyne, 2-octyne, 4-actyne, 1,7-octadiyne, 5-methyl-3-heptyne, 4-propyl-2-pentyne, 1-nonyne, benzylethyne and cyclohexylethyne.

Examples of alkenes are: ethene, propene, phenylethene, 1-butene, 2-butene, 1-pentene, 1-hexene, 1-heptene, 1-octene, 2-octene, 4-octene, cyclohexene and norbornadiene.

The acetylenically or olefinically unsaturated compound can be both an acetylene and an olefin, for example as in 3-methyl-but-3-ene-1-yne.

The unsaturated compound may be carbonylated alone or in the presence of other reactants, for example, hydrogen or a nucleophilic compound having a removable hydrogen atom. An example of a nucleophilic compound having a removable hydrogen atom is a hydroxyl-containing compound.

A hydroxyl-containing compound is preferably an alcohol, water or a carboxylic acid.

An alcohol used may be aliphatic, cycloaliphatic or aromatic and may carry one or more substituents. The alcohol preferably comprises up to 20 carbon atoms per molecule. It may be, for example, an alkanol, a cycloalkanol or a phenol. One or more hydroxyl groups may be present, in which case several products may be formed, depending on the molar ratio of the reactants used.

Examples of alkanols include methanol, ethanol, 1-propanol, 2-propanol, 1-butanol, 2-butanol, 2-methyl-propan-1-ol, and 2-methylpropan-2-ol.

Other examples of alcohols include polyvalent alcohols, in particular lower sugars such as glucose, fructose, mannose, galactose, sucrose, aldoxose, aldopentose, altrose, allose, talose, gulose, idose, ribose, arabinose, xylose, lyxose, erythrose or rhreose, cellulose, benzyl alcohol, 2,2-bis(hydroxymethyl)-1-butanol, stearyl alcohol, cyclohexanol, ethylene glycol, 1,2-propanediol, 1,4-butanediol, polyethyleneglycol, glycerol and 1,6-hexanediol.

The process according to the present invention may be carried out using a wide variety of carboxylic acids. For example, the carboxylic acids may be aliphatic, cycloaliphatic or aromatic and may carry one or more substituents, such as those named in connection with the acetylenically and olefinically unsaturated compounds.

Carboxylic acids preferably used in the process according to the invention include those containing up to 20 carbon atoms. One or more carboxylic acid groups may be present, thus allowing various products as desired, depending on the molar ratio of the reactants used. The carboxylic acids may, for example, be alkanecarboxylic acids or alkenecarboxylic acids. Examples of carboxylic acids are: formic acid, acetic acid, propionic acid, n-butyric acid, isobutyric acid, pivalic acid, n-valeric acid, n-capronic acid, caprylic acid, capric acid, lauric acid, myristic acid, palmitic acid, stearic acid, benzoic acid, o-phthalic acid, m-phthalic acid, terephthalic acid and toluic acid. Examples of alkenecarboxylic acids are acrylic acid, propiolic acid, methacrylic acid, crotonic acid, isocrotonic acid, oleic acid, maleic acid, fumaric acid, citraconic acid and mesaconic acid.

It will be appreciated that the unsaturated hydrocarbon and the hydroxyl-containing compound may be the same compound.

When an acetylenically unsaturated compound is reacted with water and carbon monoxide, an alpha,-beta-unsaturated carboxylic acid is formed. If an alcohol is used instead of water, an alpha,beta-unsaturated carboxylic ester is formed. If a carboxylic acid is used instead of water, an alpha,beta-unsaturated anhydride is formed. The alpha,beta-unsaturated product may undergo further reaction depending upon the reaction conditions employed.

It has been found that catalyst systems according to the invention are particularly useful for the carbonylation of alpha acetylenes with hydroxyl-containing compounds.

Accordingly, in a preferred aspect, therefore, the invention provides a process for the preparation of an alpha,beta-olefinically unsaturated compound, which comprises reacting an alpha acetylene with carbon monoxide and a hydroxyl-containing compound in the liquid phase in the presence of a carbonylation catalyst system as hereinbefore described.

In the process, the carbonylation catalyst system is preferably a palladium catalyst as described above, namely a catalyst system which comprises:
 a) a palladium compound,
 b) a phosphine of general formula (I), and
 c) a protonic acid.

It is not essential to use a separate solvent in the process according to the invention.

A large excess of the product or of one of the reactants, for example an alcohol, can often form a suitable liquid phase. In some cases, however, it may be desirable to use a separate solvent. Any inert solvent can be used for that purpose. Said solvent may, for example, comprise sulfoxides and sulfones, for example dimethylsulfoxide, diisopropylsulfone or tetrahydrothiophene-2,2-dioxide (also referred to as sulfolane), 2-methylsulfolane, 3-methylsulfolane, 2-methyl-4-butylsulfolane; aromatic hydrocarbons such as benzene, toluene, xylenes; esters such as methylacetate and butyrolactone; ketones such as acetone or methyl isobutyl ketone, ethers such as anisole, 2,5,8-trioxanonane (also referred to as diglyme), diphenyl ether and diisopropyl ether, and amides such as N,N-dimethylacetamide or N-methylpyrrolidone.

The process according to the present invention is conveniently effected at a temperature in the range of from 10° C. to 200° C., in particular from 20° C. to 130° C.

The process according to the invention is preferably effected at a pressure of from 1 bar to 70 bar. Pressures higher than 100 bar may be used, but are generally economically unattractive on account of special apparatus requirements.

The molar ratio of the hydroxyl-containing compound to the unsaturated hydrocarbon may vary between wide limits and generally lies within the range of 0.01:1 to 100:1.

The quantity of the Group VIII metal is not critical. Preferably, quantities are used within the range of $10^{-7}$ to $10^{-1}$ gram atom Group VIII metal per mol of unsaturated compound.

The carbon monoxide required for the process according to the present invention may be used in a practically pure form or diluted with an inert gas, for example nitrogen. The presence of more than small quantities of hydrogen in the gas stream is undesirable on account of the hydrogenation of the unsaturated hydrocarbon which may occur under the reaction conditions. In general, it is preferred that the quantity of hydrogen in the gas stream supplied is less than 5 vol %.

Another reaction which is catalyzed by catalyst systems according to the invention, and which may be regarded as a carbonylation, is the preparation of linear, alternating polyketone polymers by copolymerizing olefinically unsaturated compounds with carbon monoxide.

When polymers are desired, the catalyst system used preferably comprises a quinone. Examples of quinones are optionally substituted benzoquinones, naphthaquinones and orthoquinones. Benzoquinones are preferred especially 1,4-benzoquinone. The amount of quinone used is conveniently from 1 to 1,000 moles per gram atom of Group VIII metal (e.g. palladium), preferably from 10-5,000.

The invention will be described further by the following Examples which are illustrative in purpose and are not to be construed as limiting the scope of the invention. The term "selectivity" as used in this specification and these examples, is defined as (a/b)×100%, wherein "a" is the molar quantity of acetylenically or ethylenically unsaturated compound converted into the desired carbonylated compound, and "b" stands for the total molar quantity of unsaturated compound that has been converted. The term "reaction time" refers to the period during which reaction takes place, as evidenced by a decreasing autoclave pressure, and does not comprise an induction period which may precede the reaction period.

EXAMPLES

All preparations of phosphines were carried out under an atmosphere of argon, solvents (tetrahydrofuran, diethylether) were distilled under argon from sodium benzophenone prior to use. Unless otherwise stated, the allene content of any propyne used in the following examples was less than 0.2%.

EXAMPLE 1

Preparation of di(n-butyl)-2-pyridyl phosphine

To a magnetically stirred solution of 2.5 g phenyl(2-pyridyl)$_2$P in 20 mol tetrahydrofuran, cooled to −80° C. was added in the course of 10 min 5.9 ml of a 1.6M solution of n-butylLi in hexane. The resulting deep-red solution was allowed to warm to room temperature, and analysis of the solution by $^{31}$P NMR showed it to contain the phosphide (n-butyl)(2-pyridyl)-PLi as the only phosphorus-containing compound ($\delta_p = -16.3$ ppm).

The solution was cooled to −40° C. and a solution of 1.3 g 1-bromobutane in 10 ml tetrahydrofuran was added. The mixture was again warmed to room temperature, the solvents were removed in vacuo, and 25 ml of diethylether and 10 ml of water were added. After 10 min of stirring, the organic layer was separated and the water layer was extracted with 10 ml of ether. The organic layers were combined and the solvent was removed in vacuo (66 Pa). The resulting light-yellow liquid was analyzed by $^1$H, $^{13}$C and $^{31}$P NMR and shown to consist of a 1:1 (molar ratio) mixture of 2-phenylpyridine and (n-butyl)$_2$(2-pyridyl)P ($\delta_p = -19.5$ ppm).

EXAMPLE 2

Preparation of dimethyl 2-pyridyl phosphine and methylphenyl-2-pyridyl phosphine The method of Example 1 was repeated, except that a 1.6M solution of methyl Li in diethylether was used instead of the n-butyl Li solution, and 1.3 g iodomethane instead of the bromobutane. The reaction product was a mixture of (methyl)$_2$(2-pyridyl)P, methyl phenyl 2-pyridylP and 2-phenyl pyridine in the approximate ratio 70:30:60, from which the (methyl)$_2$(2-pyridyl)P was isolated by distillation.

The physical characteristics of the products were $\delta_p = -41.2$ ppm (dimethyl-2-pyridylphosphine) and $\delta_p = -24.1$ ppm (methylphenyl-2-pyridylphosphine).

EXAMPLE 3

Preparation of n-butyl tert-butyl 2-pyridyl phosphine

The method of Example 1 was repeated, except that 5.6 ml of a 1.7M solution of t-butyl Li in pentane was used instead of the n-butyl Li solution. The final product was identified as n-butyl t-butyl 2-pyridyl P by NMR analysis ($\delta_p = 7.4$ ppm).

EXAMPLE 4

Preparation of dimethyl 2-pyridylphosphine

The method of Example 2 was repeated, except that 1.91 g methyl(2-pyridyl$_2$P and only 0.7 g iodomethane were used. Workup as described in Example 1 afforded dimethyl 2-pyridyl phosphine, which was further purified by distillation (65% yield). ($\delta_p = -41.2$ ppm).

EXAMPLE 5

Preparation of n-butyl(4-methoxyphenyl)(2-pyridyl)phosphine)

All manipulations were carried out in an inert atmosphere (nitrogen or argon). Solvents were dried and distilled prior to use. 18 ml of a 1.6M n-butyl lithium solution in hexane was added to 30 ml diethyl ether, and the mixture was cooled to −40° C. To the stirred mixture was added in the course of 20 minutes a solution of 4.6 g 2-bromopyridine in 15 ml diethyl ether; during this addition, the temperature was kept at −40° C. After the addition, the temperature was raised to −5° C., kept there for 5 minutes, and then lowered again to −40° C. The resulting solution was added to a cooled (−40° C.) solution of 7.6 g 4-methoxyphenyl-bis(2-pyridyl)-phosphine in 30 ml THF. The mixture was warmed to room temperature. After stirring for 10 minutes, the solvents were removed in vacuo. Water (25 ml) and dichloromethane (25 ml) were added. After 5 minutes of vigorous stirring, the dichloromethane layer was separated. The water layer was extracted with two 25 ml portions of dichloromethane, the organic fractions were combined, and the solvent removed in vacuo. The residue was distilled, giving 4.7 g (60%) of (n-butyl)(4-methoxyphenyl)(2-pyridyl)phosphine as a yellowish liquid. The product was characterized by $^{31}P$ NMR: $\delta_p = -14.9$ ppm.

In this experiment, n-butyl lithium is believed to react with 2-bromopyridine to afford a mixture of n-butylbromide and 2-pyridyl lithium. Then the 2-pyridyl lithium reacts with 4-methoxy-bis(2-pyridyl)phosphine to afford 4-methoxyphenyl(2-pyridyl)lithium phosphide (and 2,2'-bipyridine). The lithium phosphide then reacts with n-butylbromide to afford (n-butyl)(4-methoxyphenyl)(2-pyridyl)phosphine.

EXAMPLE 6

Preparation of methyl di(2-pyridyl)phosphine)

All manipulations were carried out in an inert atmosphere (nitrogen or argon). Solvents were dried and distilled prior to use. 36 ml of a 1.6M n-butyl lithium solution in hexane was added to 40 ml diethyl ether, and the mixture was cooled to −40° C. To the stirred mixture was added in the course of 20 minutes a solution of 9.2 g 2-bromopyridine in 15 ml diethyl ether; during this addition, the temperature was kept at −40° C. After the addition, the temperature was raised to −5° C., kept there for 5 minutes, and then lowered again to −40° C. A solution of 3.4 g methyldichlorophosphine in 15 ml diethyl ether was added to the stirred mixture. After the addition, the mixture was warmed to room temperature, the solvents were removed in vacuo, and 50 ml water and 50 ml dichloromethane were added. After 5 minutes of vigorous stirring, the dichloromethane layer was separated. The water layer was extracted with two 50 ml portions of dichloromethane, the organic fractions were combined, and the solvent removed in vacuo. The residue was distilled, giving 4.0 g (68%) of methyl-bis(2-pyridyl)-phosphine as a yellowish liquid. The product was characterized by $^{31}P$ NMR: $\delta_p = -20.5$ ppm.

EXAMPLE 7

Preparation of methyl methacrylate by carbonylation of propyne and methanol

Methyl methacrylate was prepared as follows. A 300 ml magnetically stirred Hastelloy (Hastelloy is a registered trade mark) autoclave was successively filled with 0.025 mmol palladium(II) acetate, 1 mmol butyl(4-methoxyphenyl)(2-pyridyl)phosphine, 2 mmol p-toluenesulfonic acid, 30 ml methanol and 30 ml N-methyl-pyrrolidone (solvent). Air was evacuated from the autoclave, whereupon 25 ml of propyne was added. Subsequently, carbon monoxide was introduced to a pressure of 60 bar. The autoclave was sealed and heated to a temperature of 50° C. After a reaction time of 1½ hours at 50° C. a specimen of the contents was analyzed by means of gas-liquid chromatography. The selectivity of the conversion of propyne to methyl methacrylate was found to be 98.9%, while the mean conversion rate was calculated to be 20,000 mol propyne/gramatom Pd/hours.

EXAMPLE 8

Preparation of methyl methacrylate by carbonylation of propyne and methanol

Example 1 was repeated, but with the following differences:
  a) the ligand used was methyldi(2-pyridyl)phosphine instead of butyl(4-methoxyphenyl)(2-pyridyl)phosphine, and
  b) the reaction temperature was 80° C. instead of 50° C.

The selectivity of the conversion of propyne to methyl methacrylate was found to be 99.1%, while the mean conversion rate was calculated to be 12,500 mol propyne/gramatom Pd/hour.

COMPARATIVE EPERIMENT A

Example 8 was repeated, but with the following differences:
  a) the ligand used was phenyldi(2-pyridyl)phosphine instead of methyldi(2-pyridyl)phosphine, and
  b) the reaction time was 2 hours instead of 1½ hours.

The selectivity of the conversion of propyne to methyl methacrylate was found to be 98.3%, while the mean conversion rate was calculated to be 8,000 mol propyne/gramatom Pd/hour. The replacement of an aryl group by an aliphatic group in the organic phosphine appears to have a beneficial effect.

EXAMPLE 9

Preparation of propionic anhydride by carbonylation of ethene and propionic acid Propionic anhydride was prepared as follows. A 300 ml magnetically stirred Hastelloy (Hastelloy is a registered trade mark) autoclave was successively filled with 0.1 mmol palladium(II) acetate, 4 mmol butyl(4-methoxyphenyl)(2-pyridyl)phosphine, 2 mmol p-toluenesulfonic acid, 20 ml propionic acid and 50 ml anisole (solvent). Air was evacuated from the autoclave, whereupon ethene was blown in until a pressure of 20 bar was reached. Subsequently, carbon monoxide was introduced to a partial pressure of 30 bar. The autoclave was sealed and heated to a temperature of 90° C. After a reaction time of 5 hours at 90° C. a specimen of the contents was analyzed by means of gas-liquid chromatography. The selectivity of the conversion of ethene to propionic anhydride was found to be 99.5%, while the mean conversion rate was calculated to be 300 ml ethene/gramatom Pd/hour.

EXAMPLE 10

Preparation of methyl propionate by carbonylation of ethene and methanol

Methyl propionate was prepared as follows. Example 9 was repeated except for the difference that 50 mol methanol was added instead of the 20 ml propionic acid and 50 ml anisole. The selectivity of the conversion of ethene to methyl propionate was found to be 99.5%, while the mean conversion rate was calculated to be 200 mol ethene/gat Pd/hr.

EXAMPLE 11

Preparation of a linear alternating CO/ethane copolymer using a quinone-containing catalyst A linear, alternating CO/ethene copolymer was prepared as follows. A 250 ml magnetically stirred Hastelloy (Hastelloy is a registered trade mark) autoclave was charged with a solution of 50 ml methanol and a catalyst system comprising 0.1 mmol palladium(II) acetate, 3 mmol butyl(4-methoxyphenyl)(2-pyridyl)phosphine, 2 mmol p-toluenesulfonic acid, and 20 mmol p-benzoquinone. Air was evacuated from the autoclave, whereupon ethene was blown in until a pressure of 20 bar was reached. Subsequently, carbon monoxide was introduced to a partial pressure 30 bar. The autoclave was sealed and heated to a temperature of 110° C. After a reaction time of 3 hours at 110° C. the polymerization was terminated by cooling to room temperature and then releasing the pressure. The polymer formed was filtered off, washed with methanol and dried in vacuo at room temperature. The selectivity of the conversion of ethene to copolymer was 100°, and the yield was 0.9 g of copolymer, corresponding to a mean rate of 30 g copolymer/g Pd/hr. By means of $^{13}$C-NMR analysis it was established that the carbon monoxide/ethene copolymer prepared had a linear alternating structure and therefore consisted of units of the formula $-CO-(C_2H_4)-$.

What is claimed is:

1. A process for the carbonylation of an acetylenically or olefinically unsaturated compound, which comprises reacting an acetylenically or olefinically unsaturated compound with carbon monoxide in the presence of a catalyst system which comprises:
   a) a compound of divalent palladium,
   b) a protonic acid having a $pK_a$ (measured at 18° C. in aqueous solution) of below 6, and
   c) a monophosphine of formula $$R^2-\overset{R^1}{\underset{|}{P}}-R^3 \qquad (I)$$

wherein $R^1$ represents an aliphatic hydrocarbyl group, $R^2$ represents a pyridyl group, and $R^3$ independently has the meaning of $R^1$ or $R^2$ or represents an aryl group, in such an amount that the number of moles of monophosphine per mole of protonic acid is in the range of from 0.1 to 50.

2. The process of claim 1, in which $R^2$ represents a pyridyl group substituted by one or more substituents selected from hydroxy, halogen, alkoxy, dialkylamino, mono-, di- and trihalomethyl and alkyl groups.

3. The process of claim 1, in which $R^3$ represents a phenyl group.

4. The process of claim 3, in which the phenyl group is substituted by one or more substituents selected from hydroxy, halogen, alkoxy, dialkylamino, mono-, di- and trihalomethyl and alkyl groups.

5. The process of claim 1, in which the protonic acid has a $pK_a$ (measured at 18° C. in aqueous solution) of below 4.5.

6. The process of claim 1, in which the number of moles of monophosphine per mole of protonic acid is in the range of from 0.25 to 4.

7. The process of claim 1, in which the catalyst system further comprises a quinone.

8. The process of claim 1, wherein the unsaturated compound is an alpha acetylene and the reaction is carried out with carbon monoxide and a hydroxyl-containing compound to yield an alpha,beta-unsaturated carboxylic acid or a derivative thereof.

9. The process of claim 8, wherein the alpha acetylene is propyne and the hydroxyl-containing compound is methanol to yield methyl methacrylate.

* * * * *